(12) United States Patent
Glennon

(10) Patent No.: US 8,743,363 B1
(45) Date of Patent: Jun. 3, 2014

(54) DETECTION AND IDENTIFICATION OF SURFACES AND SURFACE CONTAMINANTS

(71) Applicant: Lockheed Martin Coherent Technologies, Inc., Louisville, CO (US)

(72) Inventor: John J. Glennon, Boulder, CO (US)

(73) Assignee: Lockheed Martin Corporation, Bethesda, MD (US)

( * ) Notice: Subject to any disclaimer, the term of this patent is extended or adjusted under 35 U.S.C. 154(b) by 0 days.

(21) Appl. No.: 13/758,925

(22) Filed: Feb. 4, 2013

Related U.S. Application Data

(60) Provisional application No. 61/595,557, filed on Feb. 6, 2012.

(51) Int. Cl.
*G01J 3/46* (2006.01)

(52) U.S. Cl.
USPC .......................................... 356/402; 356/388

(58) Field of Classification Search
USPC ......... 356/402, 388–390, 398, 456; 702/1, 22
See application file for complete search history.

(56) References Cited

PUBLICATIONS

Furstenberg, et al., "Stand-off detection of trace explosives via resonant infrared photothermal imaging," 2008, Applied Physics Letters, pp. 93, 224103.

Mukherjee, et al., "Standoff detection of explosive substances at distances of up to 150 m," 2010, Applied Optics, pp. 49, 2072.

Cho, et al., "Investigation of Standoff Explosives Detection via Photothermal/Photoacoustic Interferometry," 2011, Proceedings of SPIE vol. 8018, p. 80181T.

Van Neste, et al., "Standoff Spectroscopy of Surface Absorbed Chemicals," 2009, Analytical Chemistry, pp. 81, 1952.

Absil, et al., "Photothermal heterodyne holography of gold nanoparticles," 2010, Optics Express, pp. 18, 780.

Marron, "Photon Noise in Digital Holographic Detection," 2009, AFRL Technical Report, pp. AFRL-RD-PS-TP-2001-1006.

Marron, et al., "Atmospheric turbulence correction using digital holographic detection: experimental results," 2009, Optics Express, pp. 17, 11638.

*Primary Examiner* — Tri T Ton

(74) *Attorney, Agent, or Firm* — McDermott Will & Emery LLP

(57) ABSTRACT

Aspects of the subject technology relate to methods and systems for identifying a target material. The system includes a tunable laser, an imaging device, and a signal processor. The tunable laser is configured to intermittently direct electromagnetic radiation of at least one selected wavelength at a surface of a target material. The imaging device is configured to capture at least one "on" image of the surface when the electromagnetic radiation of the at least one selected wavelength is directed at the surface and capture at least one "off" image of the surface when electromagnetic radiation of the at least one selected wavelength is not directed at the surface. The signal processor is configured to compare, for each selected wavelength, the "on" image(s) corresponding to the selected wavelength with the "off" image(s) corresponding to the selected wavelength and identify the target material based on the comparison.

20 Claims, 3 Drawing Sheets

300

DETECTION AND IDENTIFICATION OF SURFACES AND SURFACE CONTAMINANTS

CROSS-REFERENCE TO RELATED APPLICATIONS

This application claims the benefit of priority under 35 U.S.C. §119 from U.S. Provisional Patent Application 61/595,557 filed Feb. 6, 2012, which is incorporated herein by reference in its entirety.

STATEMENT REGARDING FEDERALLY SPONSORED RESEARCH OR DEVELOPMENT

Not applicable.

FIELD

The present invention generally relates to detection and identification of materials, and more particularly to the detection and identification of surfaces or surface contaminants.

BACKGROUND

The detection and identification of materials (e.g., chemicals) at a distance is important in various applications and industries such as the health industry, the security and defense industries, or the manufacturing industry. Techniques may be used to identify dangerous or hazardous substances, detect substances that may be helpful or beneficial, or identify contaminants in a sample.

Methods for the detection of trace chemicals on surfaces at a distance (e.g., standoff detection) may fall into two categories: high power point detection and thermal emission detection. High power point detection category may include both frequency resolved Raman scattering and laser induced breakdown spectroscopy (LIBS). Both of these methods may be implemented using lasers that are capable of high peak powers. These lasers, however may be harmful to humans. Furthermore, because of the use lasers with of high peak powers and the relatively weak signals they produce for detection in the Raman scattering and LIBS methods, the sensitivity of both methods may be very dependent on the distance between the object that the lasers are directed at and a sensor detecting the signals produced by the lasers (e.g., the standoff distance). The lasers capable of high peak powers used in both of these detection techniques also may require a focused laser beam and may limit them to point detection and powers that can be unsafe for humans (and also can be destructive in the case of laser used in the LIBS method). Accordingly, in view of the use of point detection with these two methods, imaging large areas may not be efficient or practical.

Thermal emission detection methods may rely on a laser heating a chemical and detecting a temperature change via thermal emission signals. However, the practicality of deploying systems that use these methods may be hindered because the thermal emission may be weak, as only a fraction of the energy absorbed by a sample may be converted to thermal emission, especially if a contaminant is spread out over the environment. Thermal emissions are also isotropic. Accordingly, the detection of thermal emission may only be sensitive to range according to a typical $1/R^2$ manner, where R is the range. Furthermore, detection of thermal emission at wavelengths between 8-14 micrometers (µm) may require detectors that are slower and more expensive relative to technology in the visible spectrum and near infrared (NIR) spectrum (e.g., just under 800 nanometers to just over 1 micrometer). Many of the thermal emission detectors may also need to be actively cooled, which can increase the cost and power consumption of such devices. Thus, thermal emission detection may require larger receiver apertures to capture small signals even at short ranges, and the collected emission may need to be detected by expensive, slow, actively cooled long wave infrared (LWIR) detectors.

SUMMARY

Aspects of the subject technology relate to a system for identifying a target material. The system includes a tunable laser, an imaging device, and a signal processor. The tunable laser is configured to intermittently direct electromagnetic radiation of at least one selected wavelength at a surface of a target material. The imaging device is configured to capture at least one "on" image of the surface when the electromagnetic radiation of the at least one selected wavelength is directed at the surface and capture at least one "off" image of the surface when electromagnetic radiation of the at least one selected wavelength is not directed at the surface. The signal processor is configured to compare, for each selected wavelength, the at least one "on" image corresponding to the selected wavelength with the at least one "off" image corresponding to the selected wavelength and identify the target material based on the comparison.

Some aspects relate to a method for identifying a target material. The method includes directing, using a tunable laser, intermittent electromagnetic radiation of at least one selected wavelength at a surface of a target material, capturing at least one "on" image of the surface when the electromagnetic radiation of the at least one selected wavelength is directed at the surface, and capturing at least one "off" image of the surface when electromagnetic radiation of the at least one selected wavelength is not directed at the surface. The method further includes using a signal processor to compare, for each selected wavelength, the at least one "on" image corresponding to the selected wavelength with the at least one "off" image corresponding to the selected wavelength and identifying the target material based on the comparison.

The foregoing has outlined rather broadly the features of the present disclosure in order that the detailed description that follows can be better understood. Additional features and advantages of the disclosure will be described hereinafter. These and other advantages and features will become more apparent from the following description taken in conjunction with the drawings.

BRIEF DESCRIPTION OF THE DRAWINGS

For a more complete understanding of the present disclosure, and the advantages thereof, reference is now made to the following descriptions to be taken in conjunction with the accompanying drawings describing specific aspects of the disclosure.

DETAILED DESCRIPTION

Figure 1:
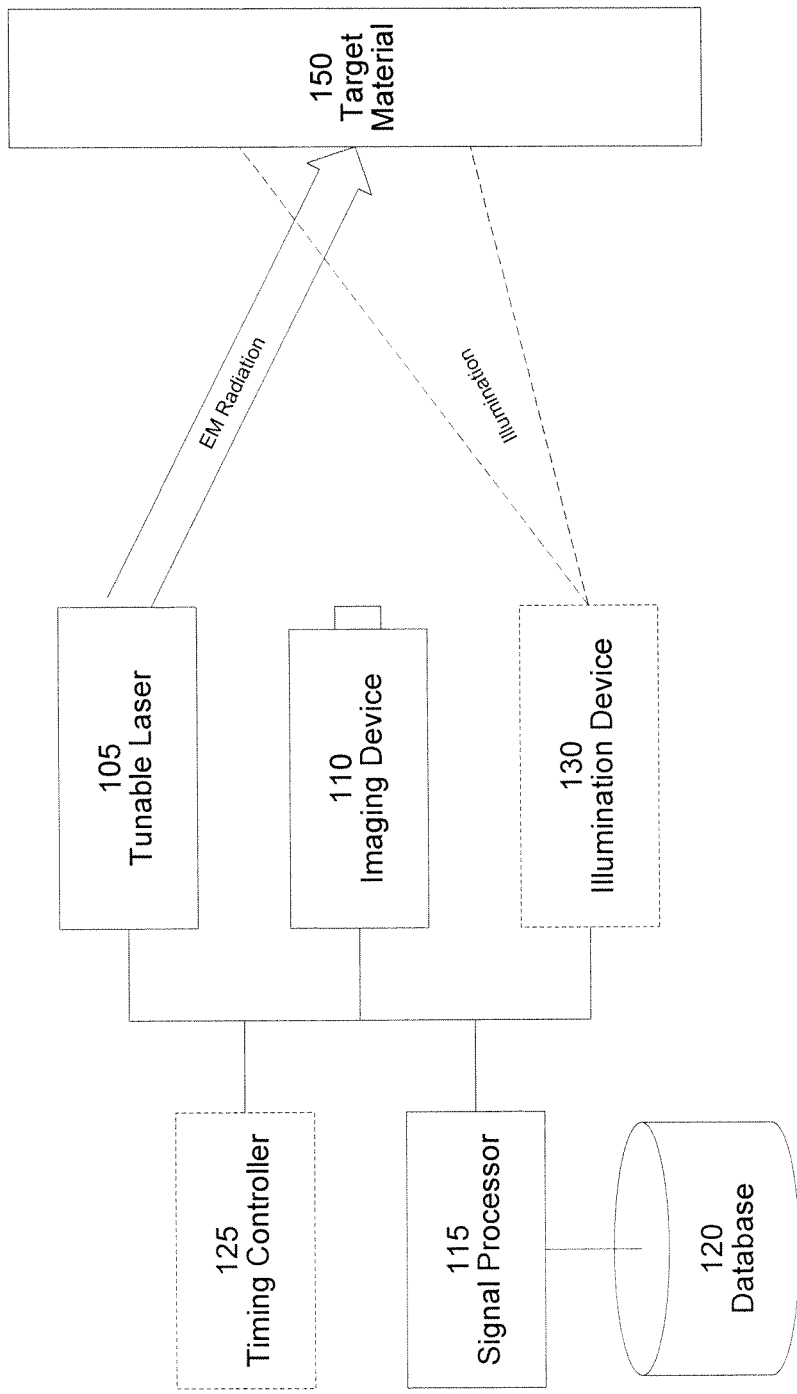
FIG. 1 is a block diagram illustrating an example system for detecting and identifying a material using a selective imaging by modulated resonant heating (SIMRH) technique, in accordance with various aspects of the subject technology.

According to various aspects of the subject technology, the chemical makeup of a material may be detected and identified using a selective imaging by modulated resonant heating (SIMRH) technique. For example, FIG. 1 is a block diagram illustrating an example system 100 for detecting and identifying a material using the SIMRH technique, in accordance with various aspects of the subject technology. The system may include a tunable laser 105, an imaging device 110, and a signal processor 115.

The tunable laser 105 (e.g., a heating laser) configured to direct electromagnetic radiation at a particular frequency onto a surface of a target material 150 being investigated. If the frequency of the electromagnetic radiation emitted by the tunable laser 105 does not correspond to a resonant frequency of a chemical species present in the surface (or anything on the surface such as a surface contaminant), the target material 150 may absorb little or no electromagnetic radiation. Although some aspects are discussed with respect to electromagnetic radiation of a particular frequency, these and other aspects may also be understood to refer to electromagnetic radiation of a corresponding wavelength (and vice versa). Furthermore, although some aspects are discussed with respect to the tunable laser 105, any other electromagnetic source may also be used. For example, a electromagnetic source capable of tuning frequency that possesses a relatively narrow spectral bandwidth may be used.

On the other hand, if the frequency (or wavelength) of the electromagnetic radiation emitted by the tunable laser 105 corresponds to a resonant frequency of a chemical species that is present in or on the target material 150, the electromagnetic radiation from the tunable laser 105 will be absorbed. The absorption of the heating laser power may induce a thermodynamic response from the surface or surface contaminant of the target material 150. The thermodynamic response may be manifested as, for example, a density change of the absorbing species, a change in the index of refraction of the absorbing species, or acoustical motion in the absorbing species. In many cases, this density change may be reversible upon cooling and may be less destructive in contrast to the other techniques.

The thermodynamic responses may be observable by using an imaging device 110. The imaging device 110 may include, for example, inexpensive commercial off-the-shelf (COTS) cameras, complementary metal-oxide-semiconductor (CMOS) image sensors, other active-pixel sensors (APS), or devices using other imaging technologies. For each frequency of electromagnetic radiation directed at the target material 150, the imaging device 110 may capture one or more images of the surface of the target material 150 while the electromagnetic radiation of the selected wavelength is directed at the surface (e.g., an "on" image) and one or more images of the surface when the electromagnetic radiation is not directed at the surface (e.g., an "off" image).

The signal processor 115 is configured to compare the one or more "on" images with the one or more "off" images. If thermodynamic responses are observable in the "on" images when compared with the "off" images, the frequency or wavelength that the tunable laser 105 directed at the target material 150 may be identified as a resonant frequency of a chemical species that is present in or on the target material 150. Other frequencies may be similarly tested to determine whether the frequency is a resonant frequency of a chemical species that is present in or on the target material 150.

The one or more resonant frequencies found for the target material 150 may be used to identify the target material 150. For example, the one or more resonant frequencies found by the signal processor 115 may be used to generate a spectral profile for the target material 150. The signal processor 115 may then identify the target material 150 by searching a database 120 containing spectral profiles for a number of known materials. According to some aspects, the database 120 may be a part of the system 100. In other aspects, however, the database 120 may be separate from the system 110 and/or the signal processor 115 may communicate with the database via a network (e.g., the Internet). The signal processor 115 may search for similar or matching spectral profiles, thereby identifying the target material 150 or components of the target material 150.

According to some aspects, the timing controller 125 maybe be configured to instruct the tunable laser 105 configured to direct electromagnetic radiation at a particular frequency onto a surface of a target material 150 being investigated at a defined interval (e.g., 2 time per second, 8 times per second, etc.). The timing controller 125 may control the interval in which the tunable laser 105 directs electromagnetic radiation by, for example, monitoring the timing and turning the laser on and off or otherwise preventing the electromagnetic radiation from teaching the target material 150 according to the timing.

By directing electromagnetic radiation at the target material 150 at defined intervals, the imaging device 110 may be able to capture thermodynamic responses that repeatedly occur. The timing controller 125 may also cause the imaging device 110 to capture images of the target material 150 at a defined interval (e.g., 8 time per second, 2 times per second, etc.). Furthermore, the tunable laser 105 and the imaging device 110 may be coordinated such that for each on-off cycle for the tunable laser 105, the imaging device 110 may capture one or more "on" images and one or more "off" images.

The signal processor 115 may then be able to more easily identify differences in the "on" images and the "off" images that are caused by absorption of electromagnetic radiation of a particular frequency. For example, the a target material 150 may thermodynamically respond to electromagnetic radiation of a particular frequency in a reversible and repeatable way. Accordingly, the signal processor 115 may target and identify changes in the images of the target material 150 that repeatedly occur at a rate that is similar or corresponds to the interval of the tunable laser 105. The signal processor 115 may use signal processing routines that focus on regions in images that capture the modulating thermodynamic responses that correspond to the on-off cycle rate of the tunable laser 105.

According to various aspects of the subject technology, one or more illumination devices 130 may also be used to aid in the detection of thermodynamic responses in the target material 150. The illumination device may emit either incoherent light (e.g., a white light source) or coherent light at a non-resonant frequency. For example, an illumination device 130 may be a probe laser configured to emit a low power beam of (single frequency) electromagnetic radiation at the target material 150.

The wavelength of the electromagnetic radiation emitted by the probe laser may be selected to have high transmission, high reflectivity off of most surfaces, and high sensitivity when detected by the imaging device 110 (e.g., a CMOS camera). Accordingly, the electromagnetic radiation emitted by the illumination device 130 is able to illuminate the surface of the target material 150 for the imaging device 110. The thermodynamic responses induced by the tunable laser's 105 electromagnetic radiation is more efficiently captured in images of the target material 150 when being illuminated by the illumination device 130.

Aspects of the subject technology have also demonstrated the ability to detect and identify substances, surfaces, thin films of liquid on surfaces, and thin films of solids on surfaces. Furthermore, as compared with some chemical detection techniques, aspects are able to extend the effective range of detection as well as obviate the use of long wavelength detection hardware. A less expensive, less range sensitive means for surface chemical detection and identification is provided.

In contrast to some techniques, the imaging device of various aspects of the subject technology may be configured to detect the thermodynamic responses caused by the target material absorbing electromagnetic radiation from the tunable laser. Therefore, electromagnetic radiation from the tunable laser need not be reflected back to the imaging device for the system to identify components of the target material as in some techniques. Accordingly, identification and detection of components of the target material may occur at greater distances and/or a less powerful (and more affordable) tunable laser may be used than if radiation from the tunable laser reflected back from the target material needed to be detected.

In some aspects, the strength of the measurable thermodynamic responses in the target material has a linear relationship with the power of the tunable laser. For example, the detected signal strength of thermodynamic responses is a target material may be increased by increasing the power of the tunable laser at a particular modulation frequency and the increase in the thermodynamic response has a linear relationship with the increase in the power of the tunable laser. Accordingly, the system is able to more effectively measure and map out the spectral profile (e.g., the absorption spectra) of components of the target material which can be compared against a library of absorption spectra. Aspects of the subject technology leverage the high throughput and sensitivity of thermal emission detection and provide various advantages over the other approaches. For example, aspects of the subject technology may allow for cheaper detection components. Since the detected signal, in some aspects, may be in the visible or near-infrared (NIR) region, the techniques may leverage the high technology readiness level (TRL) components and inexpensive components made for detection in the visible or NIR region of the spectrum.

Furthermore, some aspects of the subject technology may minimize range sensitivity. Unlike some techniques using thermal emission detection that rely on a large aperture to collect a weak, isotropically emitted signals from a surface, the subject technology may detect the backscatter from a probe beam illuminating the surface. Because backscatter signals may be many orders of magnitude higher than thermal emission signals, the probe beam can be very low power and the collecting aperture can be very small relative to the heating laser and aperture used in some thermal emission detection techniques.

Imaging sensors in the visible or NIR range used to detect the probe beam may also be higher in sensitivity than the long-wave infrared (LWIR) sensors used to detect the thermal emissions of other techniques. For these reasons, the probe beam signal can be easily detected over greater distances, thereby providing aspects of the subject technology with less range sensitivity when compared to other techniques. Instead, sensitivity may be governed by the amount of heating power that can be delivered to the surface of the target material. Thermal emission sensitivity in other techniques may depend on heating power, but also have a strong dependence on range and receiver aperture size. Furthermore, imaging at shorter wavelengths may also provide greater image resolution for the same aperture sizes. Thus, the accompanying surface images in some aspects of the subject technology can provide higher resolution than LWIR images of the same surfaces.

Figure 2:
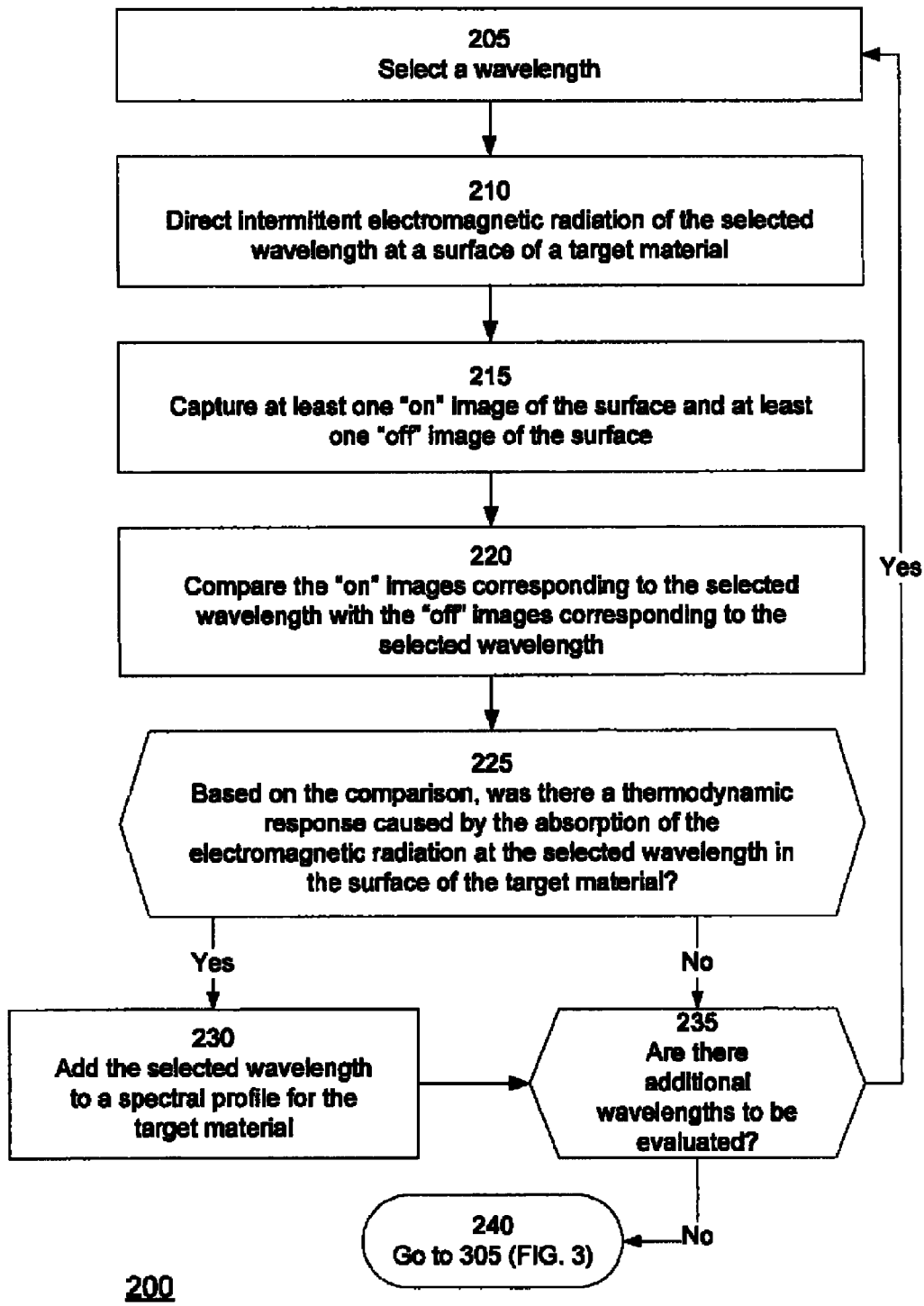
FIG. 2 is a flow chart illustrating an example process for generating a spectral profile for a target material, in accordance with various aspects of the subject technology.

FIG. 2 is a flow chart illustrating an example process 200 for generating a spectral profile for a target material, in accordance with various aspects of the subject technology. Although the blocks in process 200 are shown in a particular order, certain blocks may be executed in different orders or at the same time. In addition, although the process blocks of FIG. 2 are described with reference to the components of the system 100 in FIG. 1, the blocks are not limited to being performed by these components.

At block 205, a wavelength of electromagnetic radiation or frequency at which the tunable laser 105 is to emit is selected. At block 210, the tunable laser 105 directs intermittent electromagnetic radiation of the selected wavelength at a target material 150. As discussed above, the amplitude of the electromagnetic radiation may be modulated such that the tunable laser 105 may alternate the intensity of the electromagnetic radiation between peak energy (e.g., on) and minimum energy (e.g., no energy or off) at defined intervals.

While the tunable laser 105 is directing the electromagnetic radiation at the target material 150, the imaging device 110 may capture at least one "on" image corresponding to the peak energy being directed at the target material 150 and at least one "off" image corresponding to the minimum energy at block 215. In other aspects, additional images corresponding to other points in the modulated intervals of electromagnetic radiation may be captured. For example, the tunable laser 105 may be configured to emit fractions of peak power. Alternatively, the imaging device 110 may be configured to capture images after one or more delay periods after an "on" period or an "off" period in order to allow any changes in the characteristics of the target material 150 to stabilize.

According to some aspects, additional illumination on the target material 150 may aid the imaging device 110 in capturing images that can be used to more clearly detect any thermodynamic responses that occur in the target material 150. Illumination may be from ambient light or from an incoherent light source (e.g., a white light source). In other aspects, however, the target material 150 may be illuminated using a single frequency probe laser (e.g., a 780 nanometer continuous wave laser with <1 milliwatt of power) that enables speckle patterns to be detected by the imaging device 110.

The speckle pattern is created when the beam from the single frequency probe laser is scattered off of a rough surface and is a result of the interference of a number of waves of the same frequency, having different phases and amplitudes, which add together to give a resultant wave whose amplitude varies randomly. The speckle pattern found in the images may enable the signal processor 115 to more easily identify movement in the surface of the target material 150 caused by the absorption of electromagnetic radiation from the tunable laser 105.

According to another aspect, the target material 150 may be illuminated using a heterodyne detection technique that uses, for example, a probe laser (e.g., a single frequency probe laser) and a local oscillator. The light from the local oscillator serves as a phase reference. Light from the probe laser reflected off of the surface of the target material 150 and light from the local oscillator mix and are captured in images by the imaging device 110. The mix of light form an interference pattern (e.g., a fringe pattern) that allows the signal processor 115 to determine the relative phase of the reflected photons as compared to photons of the local oscillator, thereby enabling the signal processor 115 to detect even smaller motions in the surface of the target material 150.

At block 220, the signal processor 115 may receive the images from the imaging device 110 and compare the "on" images with the "off" images for the selected wavelength. Based on the comparison, at block 225, the signal processor 115 can determine whether there is a thermodynamic response in the target material 150 that has occurred in response to absorption of at least some electromagnetic radiation at the selected wavelength. For example, if there are detectable changes in certain regions of the "on" images when compared to the "off" images, it may indicate that materials in those regions may contain chemicals that absorb electromagnetic radiation of the selected wavelength. Changes that occur repeatedly and/or correspond with the amplitude modulation of the electromagnetic radiation emitted by the tunable laser 105 may also indicate that the material absorbs electromagnetic radiation of the selected wavelength.

If a thermodynamic response in response to the electromagnetic radiation occurred, the signal processor 115 may add the selected wavelength to a spectral profile for the target material 150. If no thermodynamic response was detected, the wavelength will not be included in the spectral profile. At block 235, if additional wavelengths of electromagnetic radiation are to be evaluated, the process may return to block 205 where a new wavelength is selected.

According to some aspects, a broad range of wavelengths may be evaluated in order to detect and identify components of the target material 150. In other aspects, a number of specific wavelengths may evaluated to determine whether the target material 150 belongs to a group of materials of interest (e.g., explosive or bio-hazardous materials, particular contaminants, etc.). If no additional wavelengths of electromagnetic radiation are to be evaluated at block 235, the process may continue at block 305 of FIG. 3.

Figure 3:
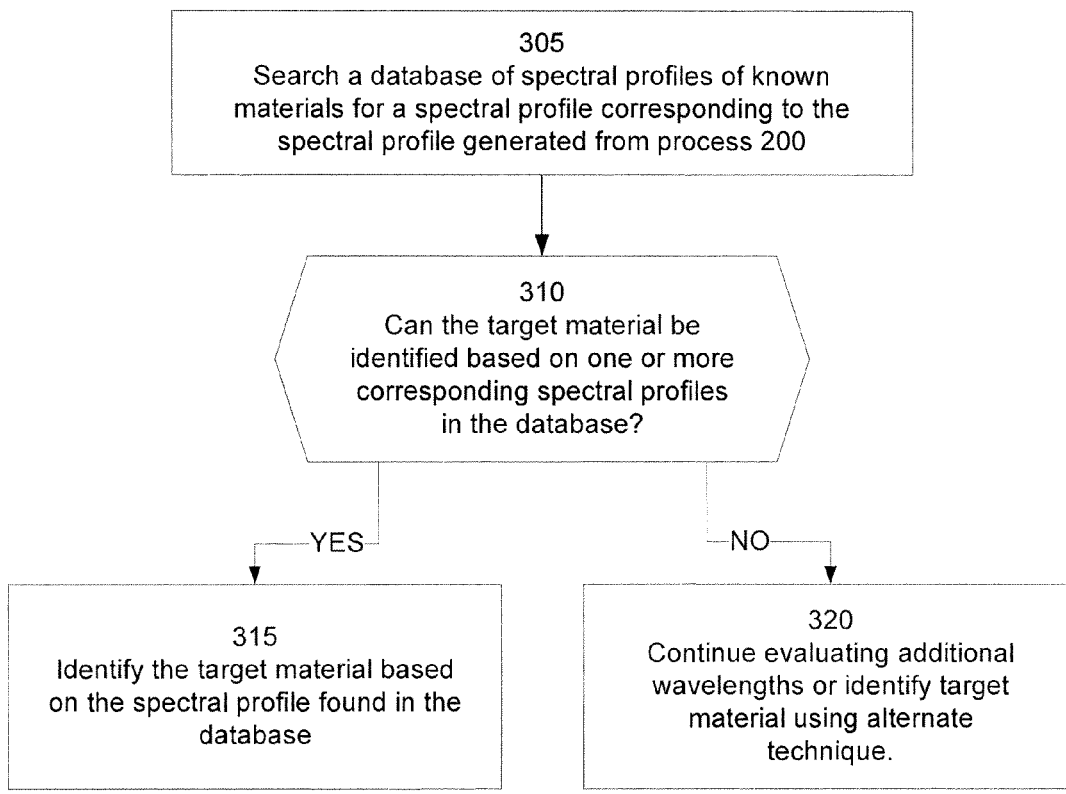
FIG. 3 is a flow chart illustrating an example process for identifying a target material based on a spectral profile, in accordance with various aspects of the subject technology.

FIG. 3 is a flow chart illustrating an example process 300 for identifying a target material based on a spectral profile, in accordance with various aspects of the subject technology. Although the blocks in process 300 are shown in a particular order, certain blocks may be executed in different orders or at the same time. In addition, although the process blocks of FIG. 3 are described with reference to the components of the system 100 in FIG. 1, the blocks are not limited to being performed by these components.

Once all of the wavelengths to be evaluated in process 200 in FIG. 2 have been evaluated, the spectral profile for the target material 150 generated by process 200 may be used to search a database 120 of spectral profiles of known materials at block 305. The signal processor 115 may search for spectral profiles that match or are similar to the spectral profile for the target material 150 generated by process 200.

In some aspects, however, the searching of the database 120 may occur in parallel with process 200. For example, the database 120 may be searched as more and more wavelengths are being added to the spectral profile for the target material 150 in process 200. In some cases, a match may be identified even before all wavelengths are evaluated in process 200.

At block 310, the signal processor 115 determines whether the target material 150 can be identified based on corresponding spectral profiles being found in the database 120. For example, only one spectral profile for a known material may match the spectral profile generated by process 200. Alternatively, more than one spectral profile of the known materials may be determined with high probability to be a component of the target material 150.

If the target material can be identified, at block 315, the signal processor 115 identifies the target material and reports the findings to a user, another component in system 100, or another device. If the target material cannot be identified, at block 320, the system 100 can continue to evaluate additional wavelengths in order to generate a more complete spectral profile for the target material 150. Alternatively, the signal processor 115 may attempt to narrow down the possibilities or otherwise identify the target material 150 using alternate techniques.

Aspects of the subject technology are able to generate spectrum profiles of components of the target material by tuning the frequency of the heating laser. In some aspects, this technique may produce spectra that agree with Fourier Transform infrared (FTIR) spectra for multiple surface components. Aspects of the subject technology have also demonstrated the ability to detect and identify surfaces, thin films of liquid on surfaces, and thin films of solids on surfaces. Furthermore, as compared with some chemical detection techniques, aspects are able to extend the effective range of detection as well as obviate the use of long wavelength detection hardware. An inexpensive, nearly range insensitive means for surface chemical detection and identification is provided.

The description of the subject technology is provided to enable any person skilled in the art to practice the various embodiments described herein. While the subject technology has been particularly described with reference to the various figures and embodiments, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these embodiments will be readily apparent to those skilled in the art, and generic principles defined herein may be applied to other embodiments. For example, instead of using a tunable laser or heating laser, some aspects may use another electromagnetic source such as a electromagnetic source capable of tuning frequency that possesses a relatively narrow spectral bandwidth. Thus, many changes and modifications may be made to the subject technology, by one having ordinary skill in the art, without departing from the scope of the subject technology.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. All structural and functional equivalents to the elements of the various embodiments described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

What is claimed is:

1. A system for identifying a target material, the system comprising:
 a tunable laser configured to intermittently direct electromagnetic radiation of at least one selected wavelength at a surface of a target material;

an imaging device configured to:
- capture at least one "on" image of the surface when the electromagnetic radiation of the at least one selected wavelength is directed at the surface, and
- capture at least one "off" image of the surface when electromagnetic radiation of the at least one selected wavelength is not directed at the surface; and a signal processor configured to:
- compare, for each selected wavelength, the at least one "on" image corresponding to the selected wavelength with the at least one "off" image corresponding to the selected wavelength, and
- identify the target material based on the comparison.

2. The system of claim 1, further comprising a database comprising spectrum profiles for a number of known materials, and wherein the identifying of the target material comprises:
- generating a spectral profile for the target material based on the comparison of the at least one "on" image with the at least one "off" image corresponding to each selected wavelength; and
- searching the database for a spectral profile of a known material corresponding to the spectral profile generated based on the comparison.

3. The system of claim 2, wherein the spectral profile for the target material is generated based on comparing "on" images with "off" images for a plurality of selected wavelengths.

4. The system of claim 1, wherein the comparing of the at least one "on" image corresponding to the selected wavelength with the at least one "off" image corresponding to the selected wavelength comprises identifying differences in the images indicating that the selected wavelength corresponds to an absorption wavelength of the target material.

5. The system of claim 4, wherein the differences in the images correspond to changes in the surface of the target material caused by thermodynamic responses of the target material to electromagnetic radiation of the selected wavelength.

6. The system of claim 5, wherein the thermodynamic responses of the target material to electromagnetic radiation of the selected wavelength comprise at least one of acoustical motion or a change in an index of refraction.

7. The system of claim 1, wherein the tunable laser is configured to intermittently direct the electromagnetic radiation at the surface at defined intervals.

8. The system of claim 7, wherein the comparing of the at least one "on" image with the at least one "off" image for each selected wavelength comprises identifying, based on the images, recurring changes in the target material that occur at a rate that corresponds to the defined intervals of the tunable laser.

9. The system of claim 7, wherein the imaging device is configured to capture images of the surface at intervals corresponding to the defined intervals of the tunable laser.

10. The system of claim 1, further comprising an illumination device configured to provide incoherent illumination of the target material.

11. The system of claim 1, further comprising an probe laser configured to provide coherent illumination of the target material at a probe frequency.

12. The system of claim 11, further comprising a local oscillator configured to provide a phase reference for the probe laser.

13. The system of claim 1, wherein the imaging device comprises a complementary metal-oxide-semiconductor (CMOS) image sensor.

14. The system of claim 1, wherein the electromagnetic radiation is at a wavelength in the visible to near-infrared range.

15. A method for identifying a target material, the method comprising:
- directing, using a tunable laser, intermittent electromagnetic radiation of at least one selected wavelength at a surface of a target material;
- capturing at least one "on" image of the surface when the electromagnetic radiation of the at least one selected wavelength is directed at the surface;
- capturing at least one "off" image of the surface when electromagnetic radiation of the at least one selected wavelength is not directed at the surface;
- comparing, for each selected wavelength, the at least one "on" image corresponding to the selected wavelength with the at least one "off" image corresponding to the selected wavelength; and
- identifying the target material based on the comparison.

16. The method of claim 15, further comprising:
- generating a spectral profile for the target material based on the comparison of the at least one "on" image with the at least one "off" image corresponding to each selected wavelength; and
- searching a database comprising spectrum profiles for a number of known materials for a spectral profile of a known material corresponding to the spectral profile generated based on the comparison.

17. The method of claim 15, wherein the comparing of the at least one "on" image corresponding to the selected wavelength with the at least one "off" image corresponding to the selected wavelength comprises identifying thermodynamic changes in the images indicating that the selected wavelength corresponds to an absorption wavelength of the target material.

18. The method of claim 15, wherein:
- the intermittent electromagnetic radiation of the at least one selected wavelength is directed at the surface of the target material at defined intervals; and
- the comparing of the at least one "on" image with the at least one "off" image for each selected wavelength comprises identifying, based on the images, recurring changes in the target material that occur at a rate that corresponds to the defined intervals of the tunable laser.

19. The method of claim 15, further comprising providing, using an probe laser, coherent illumination of the target material at a probe frequency.

20. The method of claim 19, further comprising providing, using a local oscillator, a phase reference for the probe laser.

* * * * *